(12) United States Patent
Stopek

(10) Patent No.: US 7,666,973 B2
(45) Date of Patent: Feb. 23, 2010

(54) CARBONATE COPOLYMERS

(75) Inventor: Joshua B. Stopek, Yalesville, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 201 days.

(21) Appl. No.: 11/881,851

(22) Filed: Jul. 30, 2007

(65) Prior Publication Data

US 2009/0036645 A1 Feb. 5, 2009

(51) Int. Cl.
*C08G 64/00* (2006.01)
*B32B 27/06* (2006.01)

(52) U.S. Cl. .................. 528/196; 424/78.17; 424/423; 428/480; 524/505; 524/515; 525/242; 525/326.2; 525/333.3; 525/338; 525/339; 528/198

(58) Field of Classification Search ............. 424/78.17, 424/423; 428/480; 524/505, 515; 525/242, 525/326.2, 333.3, 338, 339; 528/196, 198
See application file for complete search history.

(56) References Cited

U.S. PATENT DOCUMENTS

| | | | |
|---|---|---|---|
| 3,301,824 A | 1/1967 | Fritz et al. | |
| 4,195,167 A | 3/1980 | Knopf et al. | |
| 4,429,080 A | 1/1984 | Casey et al. | |
| 4,605,730 A | 8/1986 | Shalaby et al. | |
| 4,624,256 A | 11/1986 | Messier et al. | |
| 4,700,704 A | 10/1987 | Jamiolkowski et al. | |
| 4,791,189 A | 12/1988 | Yu | |
| 4,908,416 A * | 3/1990 | Leitz et al. ................. | 525/411 |
| 4,933,430 A | 6/1990 | Kessler et al. | |
| 4,954,593 A | 9/1990 | Vara et al. | |
| 5,252,701 A | 10/1993 | Jarrett et al. | |
| 5,550,209 A | 8/1996 | Inoue et al. | |
| 5,612,434 A | 3/1997 | Epple et al. | |
| 5,889,127 A | 3/1999 | Iiyama et al. | |
| 6,191,250 B1 | 2/2001 | Aida et al. | |
| 6,297,349 B1 | 10/2001 | Goldberg et al. | |
| 6,316,581 B1 | 11/2001 | Gross et al. | |
| 6,677,419 B1 | 1/2004 | Brock et al. | |
| 6,706,826 B1 | 3/2004 | Fujiwara et al. | |
| 6,794,484 B2 | 9/2004 | Newman, Jr. et al. | |
| 6,831,149 B2 | 12/2004 | Newman, Jr. et al. | |
| 6,875,832 B2 | 4/2005 | White et al. | |
| 6,969,749 B2 | 11/2005 | Lewandowski et al. | |
| 6,995,228 B2 | 2/2006 | Shishido et al. | |
| 2002/0165205 A1 | 11/2002 | Kubo et al. | |
| 2003/0157193 A1 | 8/2003 | McDonald et al. | |
| 2004/0014932 A1 | 1/2004 | Upshaw et al. | |
| 2004/0082755 A1 | 4/2004 | Erneta et al. | |
| 2005/0208093 A1 | 9/2005 | Glauser et al. | |
| 2006/0079624 A1 | 4/2006 | Nava et al. | |
| 2006/0100390 A1 | 5/2006 | Heise et al. | |
| 2006/0193884 A1 | 8/2006 | Stopek et al. | |
| 2007/0032666 A1 | 2/2007 | Read et al. | |
| 2008/0033106 A1 | 2/2008 | Koroskenyi et al. | |

FOREIGN PATENT DOCUMENTS

| | | |
|---|---|---|
| EP | 0 496 813 | 12/1994 |
| EP | 1 498 420 | 1/2005 |
| GB | 1 016 958 A | 1/1966 |
| WO | WO 2007/133782 A1 | 11/2007 |

OTHER PUBLICATIONS

Odian, G., "Principles of Polymerization", 3rd ed., *John Wiley & Sons, Inc.* pp. 569-573 (1991).

Iwasaki et al., "In vitro and ex vivo blood compatibility study of 2-methacryloyloxyethyl phosphorylcholine (MPC) copolymer-coated hemodialysis hollow fibers", *Journal of Artificial Organs* (2003), 6(4):260-266.

Nakabayashi et al., "Copolymers of 2-methacryloyloxyethyl phosphorylcholine (MPC) as biomaterials", *Bio-Medical Materials and Engineering* (2004), vol. 14, 345-354.

Search report from International Application No. PCT/US08/63147 dated Aug. 4, 2008.

Search Report from International Application No. PCT/US08/631479 dated Aug. 11, 2008.

Iwasaki Y; et al. "Reduced Adhesion Of Blood Cells To Biodegradable Polymers By Introducing Phosphorylcholine Moieties" *Journal Of Biomedical Materials Research Part A*, vol. 65a, 2003, pp. 164-169, XP002502022.

Meng S; et al. "Phosphorycholine end-capped poly-[epsilon]-caprolactone: A Novel Biodegradable Material With Improved Antiadsorption Property" *Journal Of Applied Polymer Science*, vol. 103, Jan. 15, 2007, pp. 989-997, XP002502023.

Watanabe J; et al. "Change in cell adhesion property on cytocompatible interface using phospholipid polymer grafted with poly(D,L-lactic acid) segment for tissue engineering" *Science and Technology of Advanced Materials*, vol. 4, 2003, pp. 539-544, XP002502024.

(Continued)

*Primary Examiner*—Terressa M Boykin

(57) ABSTRACT

Copolymer compositions are provided which include a cyclic monomer and an aromatic cyclic carbonate. The copolymer may be produced, in embodiments, by a ring-opening polymerization reaction initiated by the aromatic cyclic carbonate. The resulting copolymer may be utilized in producing medical devices, drug delivery devices, and/or coatings for medical devices.

19 Claims, No Drawings

OTHER PUBLICATIONS

Watanabe J. et al. "Cell Engineering Biointerface Focusing On Cytocompatibility Using Phospholipid Polymer With An Isomeric Oligo(Lactic Acid) Segment" *Biomacromolecules*, vol. 6, Apr. 2, 2005, pp. 1797-1802, XP002502025.

Watanabe et al. "Cytocompatible Biointerface On Poly(Lactic Acid) By Enrichment With Phosphorylcholine Groups For Cell Engineering" *Materials Science And Engineering C*, vol. 27, No. 2, Feb. 7, 2007, pp. 227-231, XP005877903 ISSN: 0928-4931.

Kristensen E M E; et al. "Photoelectron Spectroscopy Studies Of The Functionalization Of A Silicon Surface With A Phosphorylcholine-Terminated Polymer Grafted Onto (3-Aminopropyl)Trimethoxysilane" *Langmuir*, vol. 22, Oct. 12, 2006, pp. 9651-9657, XP002502026.

Zalipsky S et al.: "Long Circulating, Cationic Liposomes Containing Amino-Peg-Phosphatidylethanolamine" *FEBS Letters*, vol. 353, No. 1, Oct. 10, 1994, pp. 71-74, XP000858869 ISSN: 0014-5793.

\* cited by examiner

CARBONATE COPOLYMERS

TECHNICAL FIELD

The present disclosure provides polymer compositions which are particularly useful in the manufacture of medical devices such as sutures, staples, clips, anastomosis rings, bone plates and screws, matrices for the sustained and/or controlled release of pharmaceutically active ingredients, etc. In some embodiments, the polymer compositions may be utilized as coatings for medical devices.

DESCRIPTION OF THE RELATED ART

Polymers and copolymers of, and surgical devices made from, lactide and/or glycolide and/or related compounds are within the purview of those skilled in the art. In addition, other patents disclose surgical devices prepared from copolymers of lactide or glycolide and other monomers including caprolactone or trimethylene carbonate. For example, U.S. Pat. Nos. 4,605,730 and 4,700,704 disclose copolymers of epsilon-caprolactone and glycolide useful in making surgical articles and particularly surgical sutures. In addition, U.S. Pat. No. 4,624,256 relates to the utilization of high molecular weight caprolactone polymers as coatings for surgical sutures, while U.S. Pat. No. 4,429,080 discloses surgical articles manufactured from triblock copolymers prepared from copolymerizing glycolide with trimethylene carbonate.

The properties of bioabsorbable polymers may differ considerably depending on the nature and amounts of the comonomers, if any, employed and/or the polymerization procedures used in preparing the polymers. The selection of such polymers for use in the formation of medical devices and coatings thereon may be influenced by the properties of the various polymers, including physical properties such as the tensile strength of the polymers and the length of time before loss of strength and/or degradation occurs, and the like.

Although current medical devices and coatings thereon formed from bioabsorbable polymers may perform satisfactorily, there is room for improvement in connection with polymers having enhanced properties for the formation of medical devices and coatings on medical devices.

SUMMARY

Copolymer compositions are provided which include a cyclic monomer and an aromatic cyclic carbonate. The copolymer may be produced, in embodiments, by a ring-opening polymerization reaction initiated by the aromatic cyclic carbonate. In embodiments, methods for producing such copolymers include polymerizing at least one cyclic monomer in the presence of an aromatic cyclic carbonate to form a copolymer, and recovering the resulting copolymer.

In embodiments, a copolymer of the present disclosure may have the formula

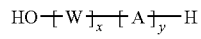

wherein W is a derivative obtained from a cyclic monomer including cyclic esters and cyclic carbonates, x is a number from about 1 to about 200, y is a number from about 1 to about 200, and A is an aromatic carbonate derivative obtained from an aromatic cyclic oligomeric carbonate of formula

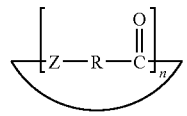

wherein R is an aromatic comprising benzene, Z comprises COO, and n is a number from about 1 to about 30.

The resulting copolymer may be utilized in producing medical devices, drug delivery devices, and/or coatings for medical devices.

DETAILED DESCRIPTION

The compositions described herein are useful for the formation of medical devices, drug delivery devices, and/or coatings on medical devices. The compositions include copolymers formed by polymerizing a cyclic monomer in the presence of a cyclic carbonate possessing an aromatic group in its ring. Suitable cyclic monomers for use in forming the copolymers of the present disclosure possess desirable properties including reasonable reaction rates under suitable reaction conditions. The resulting copolymers are biocompatible, making them suitable for the fabrication of medical devices and coatings thereon, as well as drug delivery devices.

Copolymers prepared in accordance with the present disclosure include at least one cyclic monomer as a first component of the copolymer. Suitable cyclic monomers include, for example, cyclic esters such as lactones, and cyclic carbonates. Suitable cyclic esters may include those having small rings, in embodiments 5-member rings, in other embodiments 6-member rings, and in other embodiments 7-member rings. In some embodiments, suitable cyclic esters may possess a heteroatom, such as oxygen, adjacent to the α-carbon. Suitable cyclic esters include glycolide, L(−)-lactide, D(+)-lactide, meso-lactide, p-dioxanone, 1,4-dioxan-2one, 1,5-dioxepan-2-one, epsilon-caprolactone, delta-valerolactone, gamma-butyrolactone, beta-propiolactone, and combinations thereof.

Suitable cyclic carbonates include, for example, ethylene carbonate, trimethylene carbonate, dimethyl trimethylene carbonate, 3-ethyl-3-hydroxymethyl trimethylene carbonate, propylene carbonate, trimethylolpropane monocarbonate, 4,6 dimethyl-1,3-propylene carbonate, 2,2-dimethyl trimethylene carbonate, 1,3-dioxepan-2-one, and combinations thereof.

In embodiments, the copolymers of the present disclosure include a cyclic carbonate possessing an aromatic group in its ring. Such cyclic carbonates possessing aromatic groups include, for example, oligomeric cyclic carbonates possessing an aromatic group in the ring, sometimes referred to herein as "aromatic cyclic carbonates," "aromatic cyclic oligomeric carbonates," and derivatives thereof. Such aromatic cyclic oligomeric carbonates include, for example, those disclosed in Odian, "Principles of Polymerization" $3^{rd}$ ed., John Wiley & Sons, Inc. pp. 569-573, the entire disclosure of which is incorporated by reference herein.

In some embodiments, the aromatic cyclic oligomeric carbonate may be of the following formula:

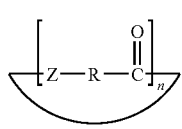

(I)

wherein R is an aromatic group such as benzene and the like; Z can be COO and the like; n may be a number from about 1 to about 30; and the remainder of the cyclic carbonate may possess from about 1 to about 30 carbon atoms, in embodiments from about 2 to about 15 carbon atoms, and may include, for example, cyclic carbonates derived from cyclic esters such as lactones, including butyrolactone, valerolactone, caprolactone, propiolactone, and combinations thereof, as well as other cyclic esters such as dioxanones, glycolide, lactide, bisphenol A, and combinations thereof.

In embodiments, the aromatic cyclic carbonate may be of the following formula:

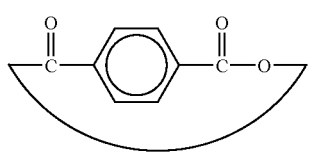

(II)

In other embodiments, aromatic cyclic carbonates may include cyclic oligomeric carbonates derived from bisphenol A derivatives including bisphenol A, 2,2'-bis(4-hydroxyphenyl)propane. Examples of such compounds include those of the following formula:

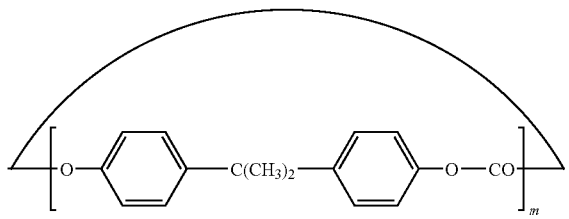

(III)

wherein m is a number from about 1 to about 30.

Copolymers of the present disclosure may be formed by combining the cyclic monomer and aromatic cyclic carbonate utilizing any method or process within the purview of those skilled in the art. In embodiments, copolymers of the present disclosure may be obtained by subjecting the cyclic monomers to a ring-opening polymerization reaction initiated by the aromatic cyclic carbonate. The result of such a polymerization reaction may include both an ester and/or carbonate derivatives from the cyclic monomer(s), and an aromatic carbonate derivative from the aromatic cyclic oligomeric carbonate. Thus, in some embodiments, the resulting copolymer may be of the following formula:

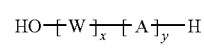

(IV)

wherein W is a derivative obtained from the cyclic monomer, in embodiments an ester or carbonate; A is the aromatic carbonate derivative obtained from the aromatic cyclic oligomeric carbonate; x is a number from about 1 to about 200, in embodiments from about 50 to about 150, and y is a number from about 1 to about 200, in embodiments from about 50 to about 150.

In some embodiments, where the aromatic cyclic oligomeric carbonate has the structure of formula II above, the resulting copolymer may have the following structure:

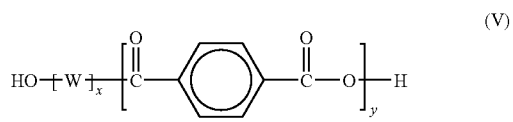

(V)

wherein W, x, and y are as defined above.

In other embodiments, where the aromatic cyclic oligomeric carbonate has the structure of formula III above, the resulting copolymer may have the following structure:

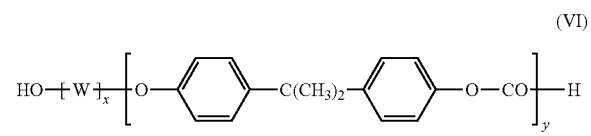

(VI)

wherein W, x and y are as defined above.

The resulting copolymer may be of random, block, or alternate configuration. It should, of course, be understood that more than one cyclic monomer can be employed to form a copolymer of the present disclosure. Where the copolymer is a block copolymer, it may have any block configuration such as AB, ABA, ABAB, ABC, ABCBA, BABA, BACAB, ABCD, and the like.

Methods for forming the copolymers of the present disclosure are within the purview of those skilled in the art, and may utilize standard reaction conditions that may be varied depending upon the cyclic monomers and aromatic cyclic oligomeric carbonates utilized to form the copolymers of the present disclosure. Cyclic monomers and aromatic cyclic carbonates may be combined in any suitable amount, in any order, to form a copolymer of the present disclosure. In some embodiments, the cyclic monomers and aromatic cyclic oligomeric carbonate(s) can be combined in the presence of a catalyst such as stannous octoate, sometimes under an inert atmosphere, such as nitrogen gas.

In some cases it may be desirable to allow the polymerization to occur under a vacuum, e.g., at a pressure less than about 1 Torr. In some embodiments it may be desirable to heat the cyclic monomers and aromatic cyclic carbonates to a suitable temperature of from about 170° C. to about 185° C., in embodiments from about 175° C. to about 180° C., in some cases to a temperature of about 178° C. The monomers may be allowed to polymerize for a suitable period of time from about 4 hours to about 6 hours, in embodiments from about 4.25 hours to about 4.75 hours.

After this time, the molten copolymer may be obtained. While not necessary, in some embodiments the copolymer of the present disclosure may be subjected to a further heat treatment by heating to a temperature of from about 100° C. to about 120° C., in embodiments from about 107° C. to about 113° C., for a period of time from about 25 hours to about 35 hours, in embodiments from about 28 hours to about 32 hours. In some cases it may be desirable for this second heat treatment to occur under a vacuum, in embodiments at a pressure less than about 1 Torr.

The derivative obtained from the cyclic monomer, in embodiments an ester or carbonate, can constitute up to about 75% by total weight of the copolymer of the present disclosure, in embodiments from about 15% to about 75% by total weight of the copolymer of the present disclosure, in other embodiments from about 30% to about 50% by total weight of the copolymer of the present disclosure. Thus, the aromatic carbonate derivative obtained from the aromatic cyclic oligomeric carbonate may constitute up to about 85% by total weight of the copolymer of the present disclosure, in embodiments from about 25% to about 85% by total weight of the copolymer of the present disclosure, in other embodiments from about 50% to about 70% by total weight of the copolymer of the present disclosure.

In addition, the copolymers of the present disclosure may be combined with other biocompatible polymers, so long as they do not interfere undesirably with the biodegradable characteristics of the copolymer. Blends of the copolymers of the present disclosure with such other polymers may offer even greater flexibility in designing the precise release profile desired for targeted drug delivery or the precise rate of biodegradability desired for structural implants. Examples of such additional biocompatible polymers include other polycarbonates; polyesters; polyorthoesters; polyamides; polyurethanes; poly(iminocarbonates); polyanhydrides; and combinations thereof.

In some embodiments, the copolymers of the present disclosure may be combined with a fatty acid component that contains a fatty acid or a fatty acid salt or a salt of a fatty acid ester. Suitable fatty acids may be saturated or unsaturated, and include higher fatty acids having more than about 12 carbon atoms. Suitable saturated fatty acids include, for example, stearic acid, palmitic acid, myristic acid and lauric acid. Suitable unsaturated fatty acids include oleic acid, linoleic acid, and linolenic acid. In addition, an ester of fatty acids, such as sorbitan tristearate or hydrogenated castor oil, may be used.

Suitable fatty acid salts include the polyvalent metal ion salts of $C_6$ and higher fatty acids, particularly those having from about 12 to 22 carbon atoms, and mixtures thereof. Fatty acid salts including the calcium, magnesium, barium, aluminum, and zinc salts of stearic, palmitic and oleic acids may be useful in some embodiments of the present disclosure. Particularly useful salts include commercial "food grade" calcium stearate which consists of a mixture of about one-third $C_{16}$ and two-thirds $C_{18}$ fatty acids, with small amounts of the $C_{14}$ and $C_{22}$ fatty acids.

Suitable salts of fatty acid esters which may be combined with the copolymers of the present disclosure include calcium, magnesium, aluminum, barium, or zinc stearoyl lactylate; calcium, magnesium, aluminum, barium, or zinc palmityl lactylate; calcium, magnesium, aluminum, barium, or zinc olelyl lactylate; with calcium stearoyl-2-lactylate (such as the calcium stearoyl-2-lactylate commercially available under the tradename VERV from American Ingredients Co., Kansas City, Mo.) being particularly useful. Other fatty acid ester salts which may be utilized include those selected from the group consisting of lithium stearoyl lactylate, potassium stearoyl lactylate, rubidium stearoyl lactylate, cesium stearoyl lactylate, francium stearoyl lactylate, sodium palmityl lactylate, lithium palmityl lactylate, potassium palmityl lactylate, rubidium palmityl lactylate, cesium palmityl lactylate, francium palmityl lactylate, sodium olelyl lactylate, lithium olelyl lactylate, potassium olelyl lactylate, rubidium olelyl lactylate, cesium olelyl lactylate, and francium olelyl lactylate.

In some embodiments it may be desirable to combine a copolymer of the present disclosure with a wax. Suitable waxes which may be utilized include polyethylene wax, ethylene copolymer wax, halogenated hydrocarbon waxes, hydrogenated vegetable oil, beeswax, caranuba wax, paraffin, microcrystalline wax, candelillia, spermacetic wax, and mixtures thereof.

In other embodiments, omega-6 fatty acids, including arachidonic acid, may be combined with the copolymers of the present disclosure.

In yet additional embodiments, phospholipids may be combined with the copolymers of the present disclosure. Suitable phospholipids include, but are not limited to, phosphatidylcholine (PC), mono-acyl phosphatidylcholine (MAPC), diacyl phosphatidylcholine (DAPC), phosphatidylserine (PS), phosphatidylethanolamine (PE), phosphatidylinositol (PI), phosphatidylglycerol (PG), plasmalogen, sphingomyelin, ceramide, ciliatin, polymers having phospholipid groups, and derivatives thereof. In some embodiments copolymers having phosphorylcholine groups may be added to the compositions of the present disclosure, such as copolymers of 2-methacryloyloxyethyl phosphorylcholine with other monomers, including methacrylates such as butyl methacrylate, benzyl methacrylate, methacryloyloxyethyl phenylcarbamate, and phenyl methacryloyloxyethyl carbamate.

In some embodiments, the copolymers of the present disclosure may also be combined with one or more bioactive agents and/or medicinal agents which may be retained in or released from the copolymers of the present disclosure. As used herein, "medicinal agent" is used in its broadest sense and includes any substance or mixture of substances that have clinical use. Consequently, medicinal agents may or may not have pharmacological activity per se, e.g., a dye.

The amount of medicinal agent present will depend upon the particular medicinal agent chosen, but in some embodiments the amount used will be from about 0.01 to about 10% by weight of the device or coating including the copolymer of the present disclosure.

Examples of classes of medicinal agents which may be combined or mixed with the copolymers of the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunosuppressants, gastrointestinal drugs, diuretics, steroids, polysaccharides, and enzymes. It is also intended that combinations of medicinal agents may be used.

Suitable antimicrobial agents which may be combined with the copolymers of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a medicinal agent in the blend or emulsion of the present disclosure.

Other medicinal agents which may be combined with the copolymers of the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; antispasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anticancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antifungals; antivirals; anticoagulants; anticonvulsants; antidepressants; antihistamines; and immunological agents.

Other examples of suitable medicinal agents which may be combined with copolymers of the present disclosure include viruses and cells, peptides (e.g., luteinizing-hormone-releasing-hormone analogues, such as goserelin and exendin) and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, enzymes (e.g., superoxide dismutase, tissue plasminogen activator), tumor suppressors, blood proteins, gonadotropins (e.g., FSH, LH, CG, etc.), hormones and hormone analogs (e.g., growth hormone, adrenocorticotropic hormone and luteinizing hormone releasing hormone (LHRH)), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; and ribozymes.

Imaging agents such as iodine or barium sulfate, or fluorine, can also be combined with the copolymers of the present disclosure to allow visualization of the surgical area through the use of imaging equipment, including X-ray, MRI, and CAT scan.

Additionally, an enzyme may be added to the copolymers of the present disclosure to increase their rate of degradation. Suitable enzymes include, for example, peptide hydrolases such as elastase, cathepsin G, cathepsin E, cathepsin B, cathepsin H, cathepsin L, trypsin, pepsin, chymotrypsin, γ-glutamyltransferase (γ-GTP) and the like; sugar chain hydrolases such as phosphorylase, neuraminidase, dextranase, amylase, lysozyme, oligosaccharase and the like; oligonucleotide hydrolases such as alkaline phosphatase, endoribonuclease, endodeoxyribonuclease and the like. In some embodiments, where an enzyme is added, the enzyme may be included in a liposome or microsphere to control the rate of its release, thereby controlling the rate of degradation of the biocompatible composition of the present disclosure. Methods for incorporating enzymes into liposomes and/or microspheres are known to those skilled in the art.

In embodiments, surfactants such as phospholipid surfactants that provide antibacterial stabilizing properties and help disperse other materials in the copolymers of the present disclosure, may also be added.

As noted above, the copolymers of the present disclosure may be used to form a medical device, a drug delivery device, or a coating for a substrate, such as a medical device.

As a structural medical device, the copolymers of the present disclosure provide a physical form having specific chemical, physical, and mechanical properties sufficient for the desired application that eventually degrade in vivo into non-toxic residues.

The copolymers described herein are non-toxic. As noted above, depending on their particular physical properties (to a large extent influenced by the nature of the cyclic monomers and aromatic cyclic carbonates from which they are prepared), the copolymers herein can be used in the fabrication in whole or in part of a variety of implantable medical devices and prostheses. Surgical and medical articles which may be prepared utilizing the copolymers of the present disclosure include, but are not necessarily limited to: burn dressings; hernia patches; medicated dressings; fascial substitutes; gauze, fabric, sheet, felt or sponge for liver hemostasis; arterial grafts or substitutes; bandages; orthopedic pins, clamps, screws, and plates; clips; staples; hooks, buttons, and snaps; bone substitutes (e.g., mandible prosthesis); intrauterine devices (e.g., spermicidal devices); draining or testing tubes or capillaries; surgical instruments; vascular implants or supports; vertebral discs; extracorporeal tubing for kidney and heart-lung machines; artificial skin; catheters; scaffoldings for tissue engineering applications; sutures; suture coatings; and the like. Applied to a suture, a coating composition including the copolymers herein results in a suture having suitable lubricity, knot tiedown, and knot security characteristics.

In embodiments, the copolymer, in combination with any optional medicinal agent, can also be melt processed using conventional extrusion or injection molding techniques, or these products can be prepared by dissolving in an appropriate solvent, followed by formation of the device, and subsequent removal of the solvent by evaporation or extraction. For example, where the copolymers of the present disclosure are used to form a medical device, the devices may be made by injection molding at temperatures and pressures within the purview of those skilled in the art. Typically, the feed for the injection molding apparatus may be a melt blend of the copolymer of the present disclosure in pellet form. The copolymer should be quite dry when being injection molded in order to avoid hydrolytic degradation during processing. After molding, the resulting surgical device prepared from the copolymers of the present disclosure can be packaged and sterilized by conventional procedures. It may be desirable to anneal the devices to remove residual stresses and strains, to stabilize the shape of the device, and to reduce or eliminate defects in the piece. Annealing may include reheating the medical device to above its glass transition temperature where chain mobility is greatest, and then slowly and gradually cooling the device. Procedures, conditions and apparatus for annealing polymeric structures are within the purview of those skilled in the art.

The copolymers of the present disclosure may also be formed into films and/or foams which, in turn, may be applied to wounds such as cuts, gashes, ulcers and burns to aid healing. Medicinal agents such as wound healing agents and antimicrobials may be incorporated to speed healing of damaged tissues. In this manner, various growth factors, antibiotics and antifungals can be combined with the copolymers of the present disclosure.

In other embodiments, the copolymers of the present disclosure may be applied as a coating to a medical device. Suitable medical devices which may be coated with the polymer of the present disclosure include, any medical device described above. In embodiments, medical devices which may be coated with a copolymer of the present disclosure include surgical needles, staples, clips and other fasteners, drug delivery devices, stents, pins, screws, prosthetic devices, implantable devices, wound dressings, anastomosis rings, and fibrous surgical articles such as sutures, prosthetic ligaments, prosthetic tendons, woven mesh, gauze, dressings, growth matrices, and the like. Fibers coated with the present compositions can be knitted or woven with other fibers, either absorbable or nonabsorbable, to form meshes or fabrics.

Copolymers of the present disclosure may be applied to a substrate as a coating, optionally combined with any of the additives described above, using any technique within the purview of those skilled in the art. Where the copolymers of the present disclosure are used as a coating for a medical device, the coating may be formed using any known technique such as, for example, extrusion, molding and/or solvent casting. The copolymer can be used alone, blended with other absorbable compositions, or blended with non-absorbable components.

In one embodiment the copolymer of the present disclosure may be applied as a coating by dissolving it in a solvent which is a non-solvent for any polymeric device to which the coating is to be applied. The solution containing the copolymer of the present disclosure may then be applied to a medical device by dipping the medical device into the solution, by passing the medical device past a brush or other applicator, or by spraying the solution onto the surface of the medical device. Suitable solvents for use in dissolving the copolymer of the present disclosure include, but are not limited to, volatile solvents such as methylene chloride, acetone, hexafluoro isopropanol (HFIP), tetrahydrofuran (THF), combinations thereof, and the like. The medical device wetted with the coating solution may then be subsequently passed through or held in a drying oven for a time and at a temperature sufficient to vaporize and drive off the solvent. If desired, the suture coating composition can optionally contain additional components, e.g., medicinal agents or similar additives described above including dyes, antibiotics, antiseptics, growth factors, anti-inflammatory agents, etc.

Where the copolymer of the present disclosure is combined with an optional additive for use as a coating, if both the copolymer and additional material are soluble in the same solvent, the appropriate amounts of the copolymer and any additive can be dissolved in the solvent and applied to the medical device to be coated as a solution. For example, the copolymers of the present disclosure may be solubilized in a dilute solution of a volatile organic solvent, e.g. acetone, methanol, ethyl acetate or toluene, and then the article can be immersed in the solution to coat its surface. Upon evaporation of the solvent, optionally at elevated temperatures, a coating of the copolymer and any additive will remain on the medical device.

Where applied in solution, the amount of solvent utilized can be from about 85% to about 99% by weight, in embodiments from about 90% to about 98% by weight of the solution utilized to apply the copolymer of the present disclosure, including any additional medicinal agents or adjuvants. In some embodiments the solvent may be present at about 95% by weight of the solution utilized to apply the copolymer of the present disclosure.

While the copolymer herein can be applied to any type of medical device, it may be especially useful as a coating for a suture. The amount of copolymer applied to a suture will vary depending upon the structure of the suture, e.g., monofilament or multifilament, the size of the suture and its composition. For multifilament sutures, the number of filaments and the tightness of the braid or twist may also influence the amount of coating.

The coating may be applied to both monofilament and multifilament braided sutures which may, in some embodiments, also be bioabsorbable. Suitable bioabsorbable monomers and polymers utilized for the sutures, including bioabsorbable braided sutures, include lactide, glycolide, trimethylene carbonate, $\epsilon$-caprolactone, caprolactam, polyesters, nylons, etc. The coating can be present in an amount from about 0.5 to about 15% (w/w) of the base suture substrate, in embodiments from about 1 to about 5% (w/w) of the base suture substrate. The thickness of the coating will depend on a number of factors, but typically can be from submicron thicknesses up to several millimeters in thickness.

In other embodiments, where the copolymer of the present disclosure and an optional additive are not completely miscible with each other or any solvents utilized to combine the two, emulsions may be formed and utilized by any means known to those skilled in the art to form medical devices including drug delivery devices or coatings for medical devices. For example, when a medicinal agent is combined with a copolymer of the present disclosure but it incompatible therewith, the medicinal agent may be placed in solution, the copolymer of the present disclosure may be placed in a separate solution, and the two combined to form an emulsion or suspension. Biocompatible dispersing agents in the form of surfactants, emulsifiers, or stablilizers may be added to the blend to assist in dispersion of the medicinal agent throughout the copolymer of the present disclosure.

Adjuvants may be added to stabilize or preserve the copolymers described above. Such adjuvants include nonionic surfactants which include alcohol ethoxylates, glycerol esters, polyoxyethylene esters, and glycol esters of fatty acids. Preferable nonionic surfactants are glycerol esters of stearic, oleic, and/or lauric acid as well as ethylene and/or diethylene glycol esters of fatty acids.

The copolymers of the present disclosure, where utilized as a coating for a medical device, may improve surface properties of the device such as, for example, cell and protein adhesion, lubricity, drug delivery, protein or DNA delivery, etc. When used as a coating, the copolymers of the present disclosure may be especially useful in preventing bacterial adhesion/colonization, infection caused by or exacerbated by the device itself, and improving the handling properties of the device.

In other embodiments, especially where the copolymer of the present disclosure is to be utilized to deliver a medicinal agent as a drug delivery device, it may be desirable to mix the medicinal agent with the copolymer of the present disclosure by processes such as ball mill, disc mill, sand mill, attritor, rotor stator mixer, ultrasonication, etc. In other embodiments, the copolymer and any optional additive can be melt blended and used to form or coat a medical device. Other methods for making and using the copolymers of the present disclosure will be readily apparent to those skilled in the art.

Where medicinal agents are combined with the copolymers of the present disclosure, the copolymers of the present disclosure may be utilized as a drug delivery device to provide site-specific release of medicinal agents which may be immediate release, delayed release or sustained release. Immediate release systems provide a drug dose instantly. Delayed release systems provide repetitive intermittent dosings of drug. Sustained release systems achieve slow release of a drug over an extended period of time and should maintain a therapeutically effective concentration of drug at the target site. Medicinal agents that are mingled with the copolymers herein typically provide delayed or sustained release therapy by diffusion from a medical device formed from the copolymers herein and/or any coating formed from the copolymers as they degrade.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A method of forming a copolymer comprising:
heating at least one cyclic monomer in the presence of an aromatic cyclic carbonate selected from the group consisting of:

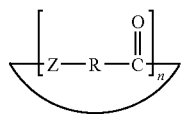

(I)

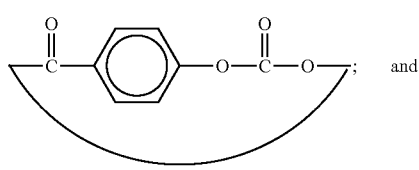

(II)

and

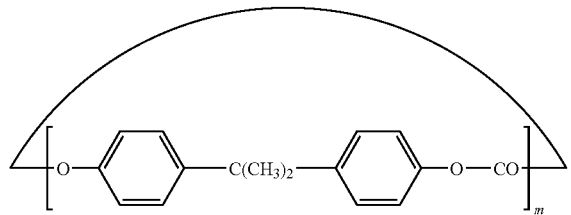

(III)

wherein R is an aromatic comprising benzene, Z comprises COO, n is a number from about 1 to about 30 and m is a number from about 1 to about 30;

allowing the at least one cyclic monomer and the aromatic cyclic carbonate to polymerize to form a copolymer; and recovering the resulting copolymer.

2. The method of claim 1, wherein the at least one cyclic monomer is selected from the group consisting of cyclic esters and cyclic carbonates.

3. The method of claim 1, wherein the at least one cyclic monomer comprises a cyclic ester selected from the group consisting of glycolide, L(−)-lactide, D(+)-lactide, meso-lactide, p-dioxanone, 1,4-dioxan-2one, 1,5-dioxepan-2-one, epsilon-caprolactone, delta-valerolactone, gamma-butyrolactone, beta-propiolactone, and combinations thereof.

4. The method of claim 1, wherein at least one cyclic monomer comprises a cyclic carbonate selected from the group consisting of ethylene carbonate, trimethylene carbonate, dimethyl trimethylene carbonate, 3-ethyl-3-hydroxymethyl trimethylene carbonate, propylene carbonate, trimethyloipropane monocarbonate, 4,6 dimethyl-1,3-propylene carbonate, 2,2-dimethyl trimethylene carbonate, and 1,3-dioxepan-2-one, and combinations thereof.

5. The method of claim 1, wherein the heating comprises heating the cyclic monomer and aromatic cyclic carbonate to a temperature of from about 170° C. to about 185° C., for a period of time from about 4 hours to about 6 hours.

6. The method of claim 1, wherein the heating comprises heating the cyclic monomer and aromatic cyclic carbonate to a temperature of from about 175° C. to about 180° C., for a period of time from about 4.25 hours to about 4.75 hours.

7. The method of claim 1, further comprising heating the copolymer to a temperature from about 100° C. to about 120° C., for a period of time ranging from about 25 hours to about 35 hours.

8. The method of claim 1, further comprising heating the copolymer to a temperature from about 107° C. to about 113° C., for a period of time ranging from about 28 hours to about 32 hours.

9. A copolymer produced by the method of claim 1.

10. A copolymer produced by the method of claim 1 having the formula

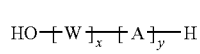

(IV)

wherein W is a derivative obtained from the cyclic monomer selected from the group consisting of esters and carbonates, A is an aromatic carbonate derivative obtained from the aromatic cyclic oligomeric carbonate, x is a number from about 1 to about 200, and y is a number from about 1 to about 200.

11. The copolymer of claim 10, wherein W comprises from about 15% to about 75% by total weight of the copolymer, and A comprises from about 20% to about 75% by total weight of the copolymer.

12. A copolymer produced by the method of claim 1 having the formula

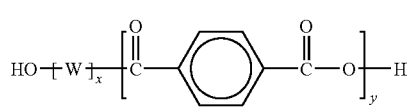

(IV)

wherein W is a derivative obtained from the cyclic monomer selected from the group consisting of esters and carbonates, x is a number from about 1 to about 200, and y is a number from about 1 to about 200.

13. A copolymer produced by the method of claim 1 having the formula

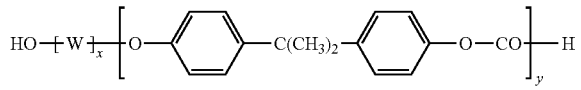

(VI)

wherein W is a derivative obtained from the cyclic monomer selected from the group consisting of esters and carbonates, x is a number from about 50 to about 150, and y is a number from about 50 to about 150.

14. A medical device comprising the copolymer produced by the method of claim 1.

15. A drug delivery device comprising the copolymer produced by the method of claim 1.

16. A coating for a medical device comprising the copolymer produced by the method of claim 1.

17. A copolymer having the formula

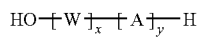

(III)

wherein W is a derivative obtained from a cyclic monomer selected from the group consisting of cyclic esters and cyclic carbonates, x is a number from about 1 to about 200, y is a number from about 1 to about 200, and A is an aromatic carbonate derivative obtained from an aromatic cyclic oligomeric carbonate of formula

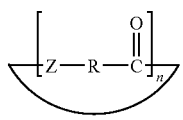

(I)

wherein R is an aromatic comprising benzene, Z comprises COO, and n is a number from about 1 to about 30.

18. The copolymer of claim 17, wherein W is a derivative obtained from a cyclic monomer selected from the group consisting of glycolide, L(−)-lactide, D(+)-lactide, meso-lactide, p-dioxanone, 1,4-dioxan-2one, 1,5-dioxepan-2-one, epsilon-caprolactone, delta-valerolactone, gamma-butyrolactone, beta-propiolactone, ethylene carbonate, trimethylene carbonate, dimethyl trimethylene carbonate, 3-ethyl-3-hydroxymethyl trimethylene carbonate, propylene carbonate, trimethyloipropane monocarbonate, 4,6 dimethyl-1,3-propylene carbonate, 2,2-dimethyl trimethylene carbonate, and 1,3-dioxepan-2-one, and combinations thereof, and A is an aromatic carbonate derivative obtained from an aromatic cyclic carbonate selected from the group consisting of formula

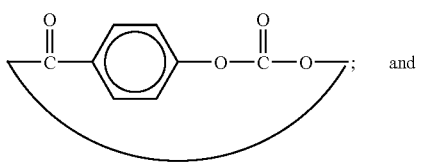

(II)

and

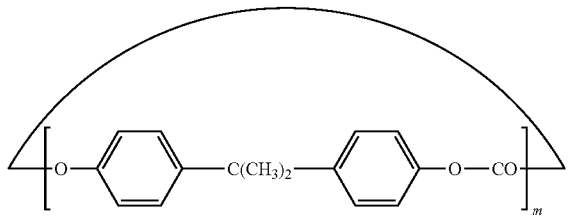

(III)

wherein m is a number from about 1 to about 30.

19. The copolymer of claim 17, wherein W comprises from about 15% to about 75% by total weight of the copolymer, and A comprises from about 20% to about 75% by total weight of the copolymer.

* * * * *